US00PP19855P2

(12) United States Plant Patent
Holtmaat

(10) Patent No.: US PP19,855 P2
(45) Date of Patent: Mar. 24, 2009

(54) *ASTILBE* PLANT NAMED 'VALERY'

(50) Latin Name: *Astilbe chinensis*
Varietal Denomination: Valery

(75) Inventor: Henricus Maria Joseph Holtmaat, Zuidwolde (NL)

(73) Assignee: Maatschap Holtmaat, Zuidwolde (NL)

( * ) Notice: Subject to any disclaimer, the term of this patent is extended or adjusted under 35 U.S.C. 154(b) by 0 days.

(21) Appl. No.: 11/983,749

(22) Filed: Nov. 12, 2007

(51) Int. Cl.
*A01H 5/00* (2006.01)

(52) U.S. Cl. ..... Plt./407
(58) Field of Classification Search ..... Plt./407
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Astilbe* plant named 'Valery', characterized by its compact, upright and sturdy plant habit; strong and healthy dark green-colored foliage; freely flowering habit; red purple-colored flowers arranged on thick flowering stems; and good garden performance.

3 Drawing Sheets

Botanical designation: *Astilbe chinensis.*
Cultivar denomination: 'Valery'.

BACKGROUND OF THE INVENTION

The present invention relates to a new and distinct cultivar of *Astilbe,* botanically known as *Astilbe chinensis* and hereinafter referred to by the name 'Valery'.

The new *Astilbe* is a product of a planned breeding program conducted by the Inventor in Zuidwolde, The Netherlands. The objective of the breeding program was to create new compact and sturdy *Astilbe* cultivars with numerous attractive flowers.

The new *Astilbe* originated from an open-pollination in 1999 in Zuidwolde, The Netherlands, of an unidentified selection of *Astilbe chinensis,* not patented, as the female, or seed, parent with an unknown selection of *Astilbe chinensis,* as the male, or pollen, parent. The new *Astilbe* was discovered and selected by the Inventor as a single flowering plant within the progeny of the stated open-pollination in a controlled environment in Zuidwolde, The Netherlands in 2002.

Asexual reproduction of the new *Astilbe* by divisions in a controlled environment in Zuidwolde, The Netherlands since 2004, has shown that the unique features of this new *Astilbe* are stable and reproduced true to type in successive generations.

SUMMARY OF THE INVENTION

The cultivar Valery has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Valery'. These characteristics in combination distinguish 'Valery' as a new and distinct cultivar of *Astilbe:*

1. Compact, upright and sturdy plant habit.
2. Strong and healthy dark green-colored foliage.
3. Freely flowering habit.

4. Red purple-colored flowers arranged on thick flowering stems.
5. Good garden performance.

Plants of the new *Astilbe* and the female parent selection differ primarily in flower coloration and plant height.

Plants of the new *Astilbe* can be compared to plants of the cultivar Vision in Red, disclosed in U.S. Plant Pat. No. 11,965. In side-by-side comparisons conducted in Zuidwolde, The Netherlands, plants of the new *Astilbe* and the cultivar Vision in Red differed in the following characteristics:

1. Plants of the new *Astilbe* were compact than plants of the cultivar Vision in Red.
2. Plants of the new *Astilbe* and the cultivar Vision in Red differed in leaf and flower coloration.
3. Plants of the new *Astilbe* had fewer flowering stems than plants of the cultivar Vision in Red.

BRIEF DESCRIPTION OF THE PHOTOGRAPHS

The accompanying colored photographs illustrate the overall appearance of the new *Astilbe,* showing the colors as true as it is reasonably possible to obtain in colored reproductions of this type. Colors in the photographs may differ slightly from the color values cited in the detailed botanical description which accurately describe the colors of the new *Astilbe.*

The photograph on the first sheet comprises a side perspective view of a typical flowering plant of 'Valery' grown in a container.

The photograph on the second sheet is a close-up view of a typical inflorescence of 'Valery'.

The photograph at the top of the third sheet is a close-up view of typical flowers of 'Valery'.

The photograph at the bottom of the third sheet is a close-up view of the upper surface of a typical leaf of 'Valery'.

DETAILED BOTANICAL DESCRIPTION

The aforementioned photographs and following observations, measurements and values describe plants grown in containers in Zuidwolde, The Netherlands, under commercial practice during the summer autumn in an outdoor nursery with day temperatures ranging from 12° C. to 32° C. and night temperatures ranging from 6° C. to 18° C. Plants had been growing for about one year when the photographs and description were taken. In the following description, color references are made to The Royal Horticultural Society Colour Chart, 2001 Edition, except where general terms of ordinary dictionary significance are used.

Botanical classification: *Astilbe chinensis* cultivar Valery.

Parentage:

*Female, or seed, parent.*—Unidentified selection of *Astilbe chinensis,* not patented.

*Male, or pollen, parent.*—Unknown selection of *Astilbe chinensis,* not patented.

Propagation:

*Type.*—By divisions.

*Time to initiate roots, summer.*—About 10 days at 22° C.

*Time to initiate roots, winter.*—About 20 days at 10° C.

*Time to produce a rooted plant.*—About six weeks at 20° C. to 25° C.

*Root description.*—Fibrous, medium in thickness; yellowish white in color.

*Rooting habit.*—Moderately branching.

Plant description:

*Plant form/habit.*—Herbaceous perennial. Upright and sturdy plant habit; roughly narrowly triangular. Flowering stems and leaves basal; dense and bushy growth habit; moderately vigorous growth habit. Freely flowering habit with numerous flowers on branched panicles with thick peduncles.

*Growth rate.*—Moderate; from divisions, about 20 weeks are required to produce fully-grown flowering plants.

*Plant height* (*soil level to top of foliar plane*).—About 24 cm.

*Plant height* (*soil level to top of inflorescences*).—About 53 cm.

*Plant width* (*spread*).—About 56 cm.

*Stem description.*—Length: About 23.8 cm. Diameter: About 5 mm. Internode length: About 4 cm. Strength: Strong. Texture: Sparsely pubescent. Color: 152A to 152B flushed with 178B.

Foliage description:

*Arrangement.*—Alternate; biternately compound.

*Leaf length* (*excluding petiole*).—About 18.1 cm.

*Leaf width.*—About 22.1 cm.

*Lateral leaflet length.*—About 4.2 cm.

*Lateral leaflet width.*—About 2.6 cm.

*Terminal leaflet length.*—About 4.8 cm.

*Terminal leaflet width.*—About 3.1 cm.

*Lateral and terminal leaflet shape.*—Ovate.

*Lateral and terminal leaflet apex.*—Acute.

*Lateral and terminal leaflet base.*—Obtuse to rounded.

*Lateral and terminal leaflet margin.*—Biserrate.

*Lateral and terminal leaflet texture, upper and lower surfaces.*—Sparsely pubescent; slightly rough.

*Lateral and terminal leaflet venation pattern.*—Pinnate.

*Lateral and terminal leaflet color.*—Developing leaves, upper surface: Slightly darker than 143A. Developing leaves, lower surface: 144A. Fully expanded leaves, upper surface: 137A; venation, 138B. Fully expanded leaves, lower surface: 138A; venation, 146C to 146D.

*Leaf petiole length.*—About 11 cm.

*Leaf petiole diameter.*—About 3 mm.

*Leaflet petiole length.*—About 4.7 cm.

*Leaflet petiole width.*—About 3 mm.

*Leaf and leaflet petiole texture, upper and lower surfaces.*—Smooth, glabrous.

*Leaf and leaflet petiole color, upper and lower surfaces.*—Towards the apex, 178B; towards the base, close to 152B to 152C.

Flower description:

*Flower type/habit.*—Numerous single rotate flowers arranged on branched panicles; flowers face upright, outward or downward depending on position on the panicle. Panicles very narrowly conical in shape. Freely and uniformly flowering habit with about 1,000 flowers develop per inflorescence; typically four panicles develop per plant. Flowers sessile.

*Fragrance.*—Faintly fragrant; sweet.

*Natural flowering season.*—Continuously flowering for about six weeks during the summer and late summer in The Netherlands.

*Postproduction longevity.*—Flowers last about ten days on the plant. Flowers persistent.

*Flower buds.*—Height: About 2 mm. Diameter: About 1.5 mm. Shape: Broadly ovate. Color: 183C to 183D.

*Inflorescence height.*—About 29.2 cm.

*Inflorescence diameter.*—About 12.8 cm.

*Flower diameter.*—About 5 mm.

*Flower depth.*—About 5 mm.

*Petals.*—Quantity per flower: Typically five in a single whorl. Length: About 4 mm. Lobe width: About 0.5 mm. Shape: Lanceolate. Apex: Acute. Margin: Entire. Texture, upper and lower surfaces: Smooth, glabrous. Color: Developing petals, upper and lower surfaces: Close to 85A to 85B. Fully expanded petals, upper and lower surfaces: Close to 85A to 85B; color becoming closer to 85A with development.

*Sepals.*—Quantity per flower: Typically five in a single whorl, fused towards the base; campanulate calyx. Length: About 2.5 mm. Width: About 1 mm. Shape: Ovate. Apex: Acute. Margin: Entire. Texture, upper and lower surfaces: Smooth, glabrous. Color, developing sepals, upper and lower surfaces: Close to 183C to 183D. Color, fully expanded sepals, upper and lower surfaces: Close to 72B to 72C; towards the base, close to 65D.

*Peduncles.*—Length: About 28.8 cm. Diameter: About 4 mm. Angle: Mostly erect. Strength: Strong. Texture: Densely pubescent. Color: Close to 152A to 152B flushed with 178B.

*Reproductive organs.*—Stamens: Quantity per flower: Typically ten; anthers basifixed. Filament length: About 2 mm. Anther shape: Ovate. Anther length: About 0.2 mm. Anther color: Slightly more grey than 94C. Pollen amount: Scarce to moderate. Pollen color: Close to 155D. Pistils: Quantity per flower: Typically two. Pistil length: About 1 mm. Stigma shape: Club-shaped. Stigma color: 72B to 72C. Style length: About 0.9 mm. Style color: Close to 72C. Ovary color: Close to 72D.

*Seed/fruit.*—Seed and fruit development have not been observed.

Disease/pest resistance: Plants of the new *Astilbe* have not been noted to be resistant to pathogens and pests common to *Astilbe*.

Garden performance: Plants of the new *Astilbe* have been observed to have good garden performance and tolerate rain, wind and high temperatures of about 35° C. Plants of the new *Astilbe* have been observed to be hardy to USDA Zone 5.

It is claimed:

1. A new and distinct *Astilbe* plant named 'Valery' as illustrated and described.

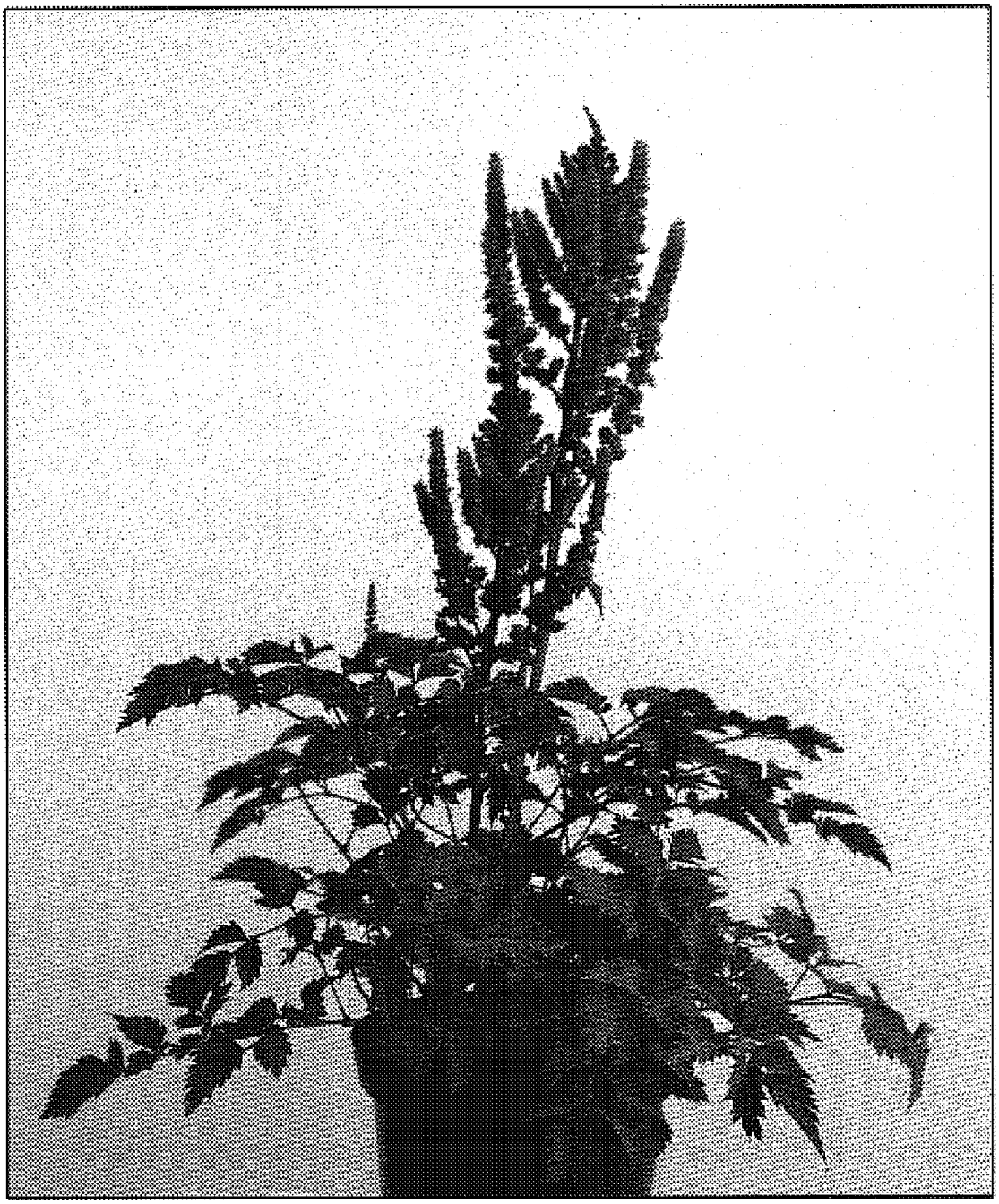

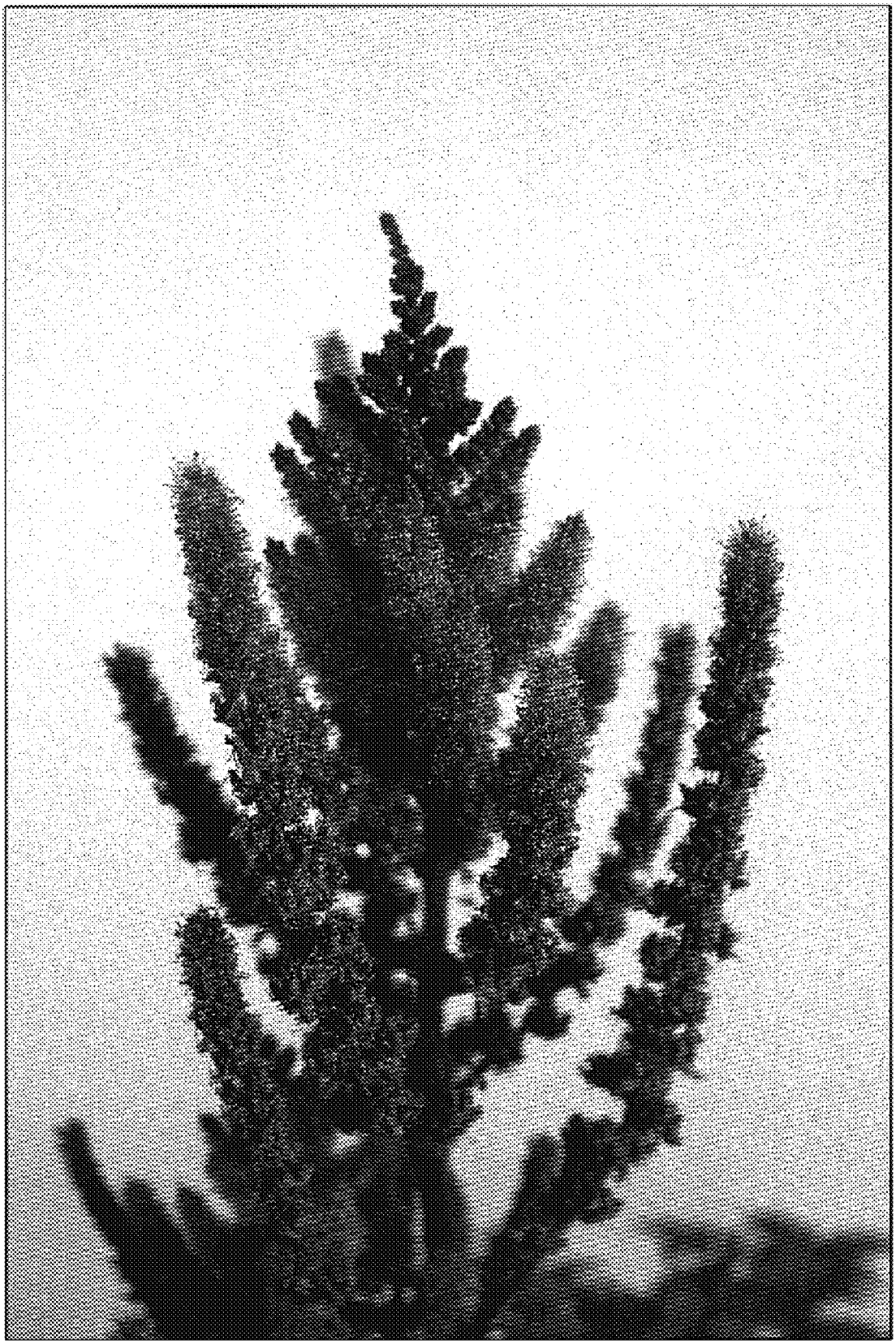

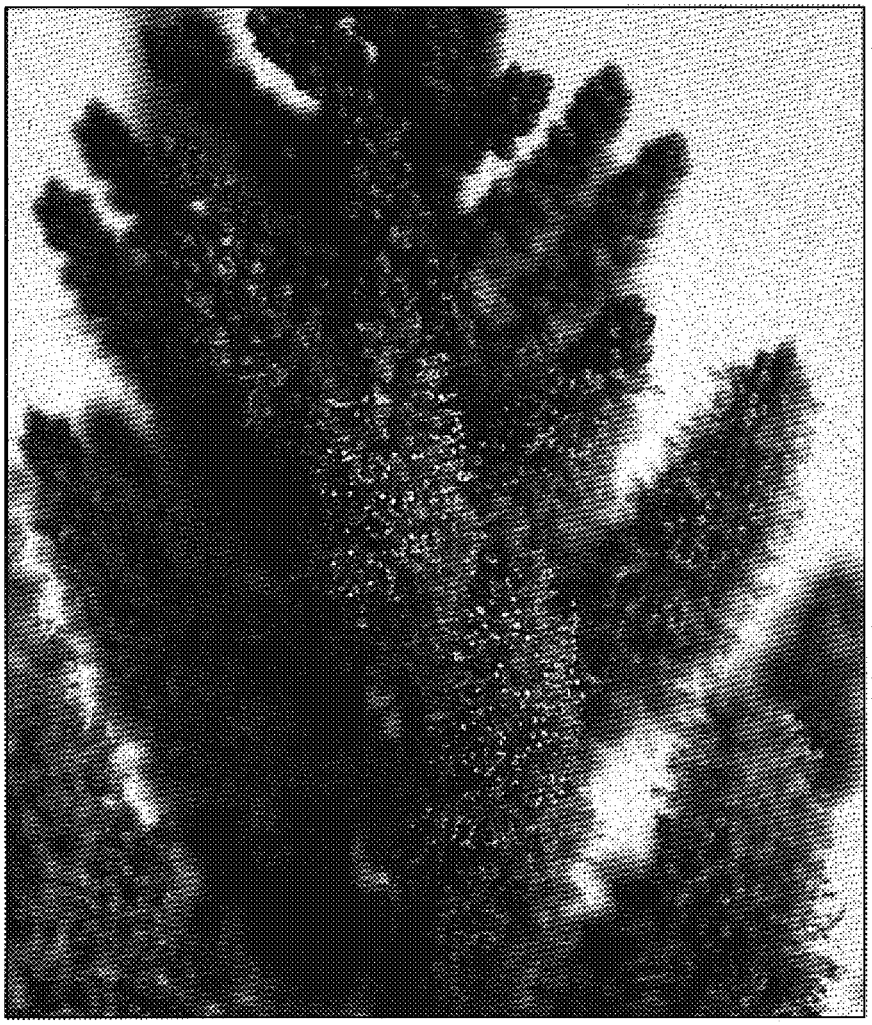
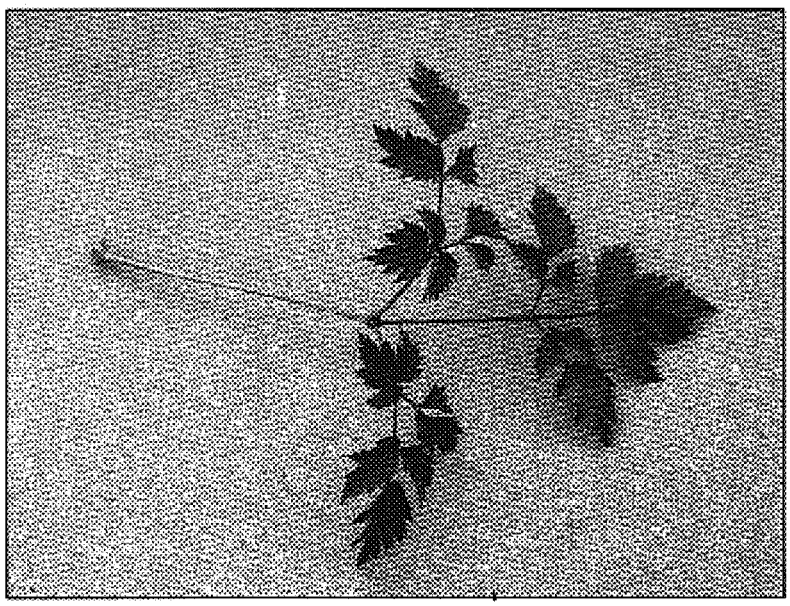

* * * * *